(12) United States Patent
Davis

(10) Patent No.: US 6,221,065 B1
(45) Date of Patent: Apr. 24, 2001

(54) SELF-PRIMING NEEDLE-FREE "Y"-ADAPTER

(75) Inventor: Ralph L. Davis, Genoa City, WI (US)

(73) Assignee: Filtertek Inc., Hebron, IL (US)

( * ) Notice: Subject to any disclaimer, the term of this patent is extended or adjusted under 35 U.S.C. 154(b) by 0 days.

(21) Appl. No.: 09/055,142

(22) Filed: Apr. 3, 1998

(51) Int. Cl.$^7$ .................. A61M 25/16; A61M 25/18; A61M 39/02

(52) U.S. Cl. .................. 604/539; 604/284; 604/905; 604/533

(58) Field of Search .................. 604/284, 256–7, 604/83, 283, 236, 247, 249, 250, 905, 533, 539; 137/903

(56) References Cited

U.S. PATENT DOCUMENTS

| | | | |
|---|---|---|---|
| 5,201,725 | * | 4/1993 | Kling .................................. 604/284 |
| 5,356,375 | * | 10/1994 | Higley .................................. 604/30 |
| 5,618,268 | | 4/1997 | Raines et al. . |
| 5,676,346 | * | 10/1997 | Leinsing ............................ 251/149.1 |
| 5,782,816 | * | 7/1998 | Werschmidt et al. ................ 604/256 |

FOREIGN PATENT DOCUMENTS 0 684 050   11/1995   (EP) .

* cited by examiner

Primary Examiner—Richard K. Seidel
Assistant Examiner—Jennifer Maynard
(74) Attorney, Agent, or Firm—Brinks Hofer Gilson & Lione

(57) ABSTRACT

In preferred aspects, the present invention comprises a self-priming needle-free "Y"-adapter for use with intravenous delivery systems. The "Y"-adapter comprises a "Y"-shaped housing having an inlet passageway, an outlet passageway, and an injection access passageway. Each of the three passageways has an interior end and an exterior end. An inlet port is located at the exterior end of the inlet passageway. An outlet port is located at the exterior end of the outlet passageway. An injection access port is located at the exterior end of the injection access passageway. A needle-free access device is also located in the injection access passageway adjacent to the injection access port. The interior ends of the passageways are in fluid communication and intersect with each other. In addition, the injection access passageway comprises a non-circular cross-section near its interior end. The non-circular cross-section of the interior end of the injection access passageway assists in priming the "Y"-adapter.

14 Claims, 2 Drawing Sheets

SELF-PRIMING NEEDLE-FREE "Y"-ADAPTER

BACKGROUND OF THE INVENTION

The present application relates to "Y"-adapters for use with liquid flow and administrative apparatus for medical purposes. In particular, the present application relates to a self-priming needle-free "Y"-adapter for use with intravenous delivery systems.

An intravenous ("IV") delivery system, such as a low volume drug infuser, is commonly used to administer fluids such as saline solution or blood plasma to a patient. One end of the IV set tubing is connected to the fluid to be administered to the patient. The other end of the IV set tubing is connected to a needle which is inserted into the vein of the patient. The IV delivery system ordinarily includes a flow control device which regulates the rate of flow of the fluid being administered. The IV delivery system may also include other devices such as drip chambers, filters, or air eliminators.

The IV delivery system may also include an adapter or connector through which additional fluid medications can be administered to the patient, thereby reducing or eliminating the need to administer separate injections to the patient. The adapter is typically "Y"-shaped having three ends. Two of the ends of the "Y"-adapter are connected to the IV set tubing to permit unobstructed flow of the IV fluid through the adapter. The third end of the "Y"-adapter typically comprises a septum through which a hypodermic needle can be passed to inject the fluid medication into the adapter. The fluid medication mixes with, and is consequently transported to the patient by, the IV fluid.

In recent years, there has been an effort to reduce the use of hypodermic needles to avoid needle-stick accidents. These are not only painful, but could cause serious disease or complications in the needle-stick victim if the needle is contaminated. Thus, it is therefore desirable to provide an IV tubing adapter which utilizes a needle-free access port in lieu of a septum. Several types of needle-free access devices are described in U.S. Pat. No. 5,360,413. However, prior attempts to incorporate a needle-free access port into a typical "Y"-adapter have been unsuccessful. For example, the interior configuration of such devices often results in trapped air within the device when the device is initially connected to the IV set tubing. This trapped air may inhibit the flow of fluids through the device. The trapped air may also inadvertently enter the flow path of the IV fluid, subsequently entering the blood stream of the patient. The introduction of air bubbles into the blood stream may pose serious medical complications for the patient. It is therefore desirable to provide a needle-free "Y"-adapter which is self-priming.

SUMMARY OF THE INVENTION

In preferred aspects, the present invention comprises a needle-free "Y"-adapter for use with intravenous delivery systems. The "Y"-adapter comprises a "Y"-shaped housing having an inlet passageway, an outlet passageway, and an injection access passageway. Each of the three passageways has an interior end and an exterior end. The interior ends of the passageways are in fluid communication and intersect with each other. In addition, the injection access passageway comprises a non-circular cross-section near its interior end.

An inlet port is located at the exterior end of the inlet passageway. An outlet port is located at the exterior end of the outlet passageway. An injection access port is located at the exterior end of the injection access passageway. A needle-free access device is also located in the injection access passageway adjacent to the injection access port.

The non-circular cross-section of the interior end of the injection access passageway assists in priming the "Y"-adapter. In the preferred embodiment, the portion of the injection access passageway adjacent to the inlet and outlet passageways has an elliptical cross-section. This configuration reduces the possibility that air will be trapped inside the "Y"-adapter housing when the "Y"-adapter is initially connected to the IV set tubing.

These and other advantages, as well as the invention itself, will become apparent in the details of construction and operation as more fully described and claimed below. Moreover, it should be appreciated that several aspects of the invention can be used with other types of medical devices and devices for intravenous delivery systems.

DETAILED DESCRIPTION OF THE DRAWINGS AND PREFERRED EMBODIMENTS OF THE INVENTIONS

While the present invention will find application in all types "Y"-adapters, the preferred embodiment of the invention is described in conjunction with the needle-free "Y"-adapter of FIGS. 1–4.

Figure 1:
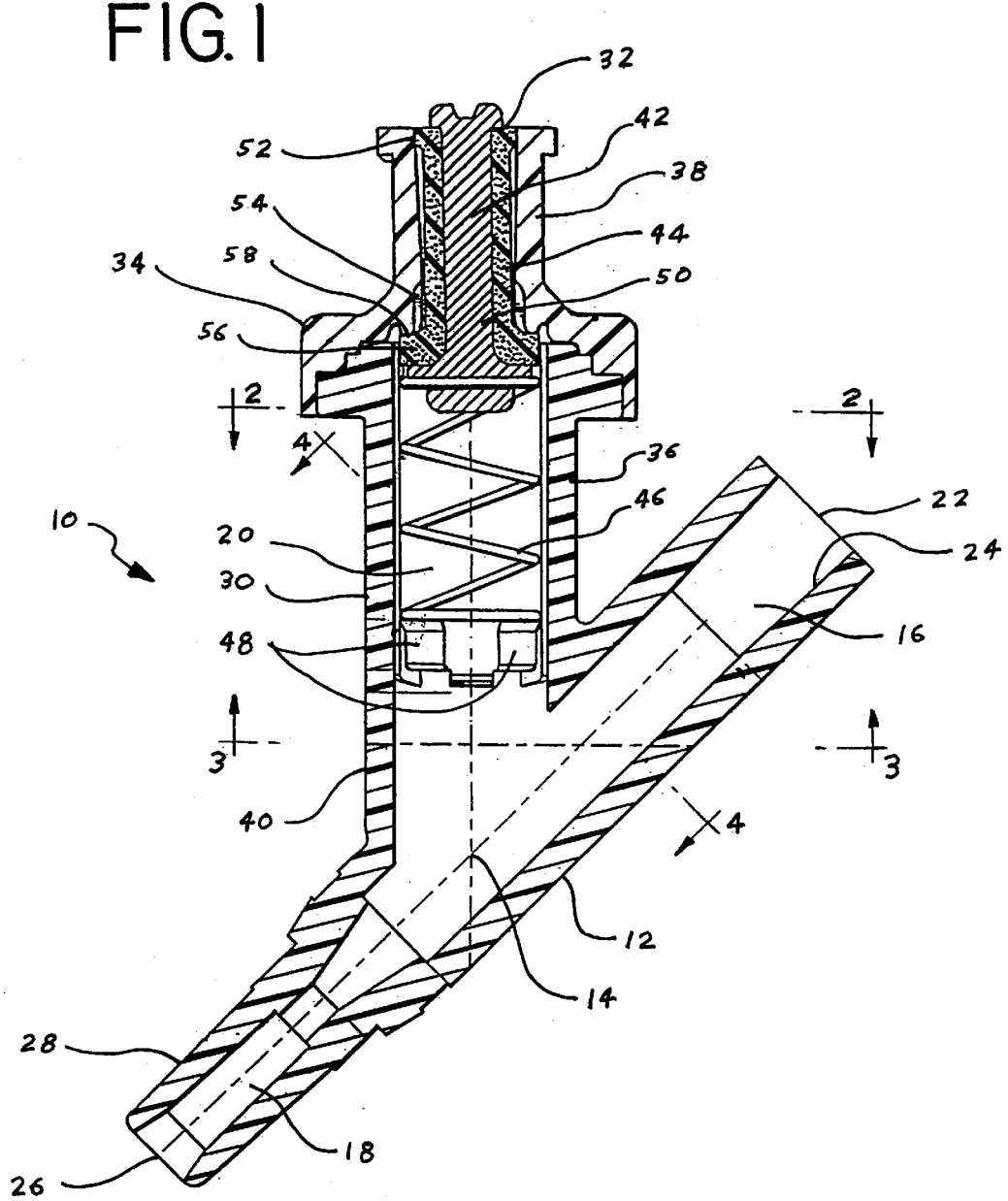
FIG. 1 is a cross-sectional view of a embodiment of a self-priming needle-free "Y"-adapter of the present invention.

As best seen in FIG. 1, the needle-free "Y"-adapter 10 comprises a "Y"-shaped housing 12 having three interior passageways which intersect near the central portion of the housing. The intersection of the central axis of these three passageways is called the "Y"-site 14. The three passageways are designated as the inlet passageway 16, the outlet passageway 18, and the injection access passageway 20, respectively.

Figure 4:
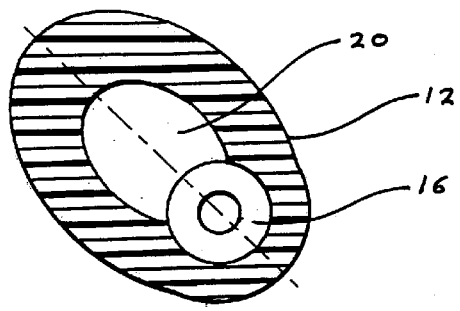
FIG. 4 is a cross-sectional view taken along line 4—4 of FIG. 1.

The inlet passageway 16 is formed by the interior surface of the "Y"-adapter housing 12. As best seen in FIG. 4, the inlet passageway 16 has a central axis and a circular cross-section. Referring to FIG. 1, the exterior end of the inlet passageway 16 terminates in an inlet port 22. The inlet port 22 is configured and sized to permit the insertion of standard IV set tubing (not shown). In the embodiment shown, the interior surface 24 of the "Y"-adapter housing 12 is tapered inwardly from the inlet port 22 so as to form a standard female luer. The taper, or female luer, permits a force fit seal to be created between the interior surface 24 of the housing 12 and the exterior surface of the IV set tubing when the IV set tubing is inserted through the inlet port 22 and into the inlet passageway 16.

The outlet passageway 18 is formed by the interior surface of the "Y"-adapter housing 12. As best seen in FIG. 4, the outlet passageway 18 has a central axis and a circular cross-section. Referring to FIG. 1, the exterior end of the outlet passageway 18 terminates in an outlet port 26. The outlet port 26 is configured and sized to permit the connection to standard IV set tubing (not shown). In the embodiment shown, the exterior surface 28 of the "Y"-adapter housing 12 is tapered towards the outlet port 26 to form a standard male luer for insertion into the IV set tubing.

Figure 2:
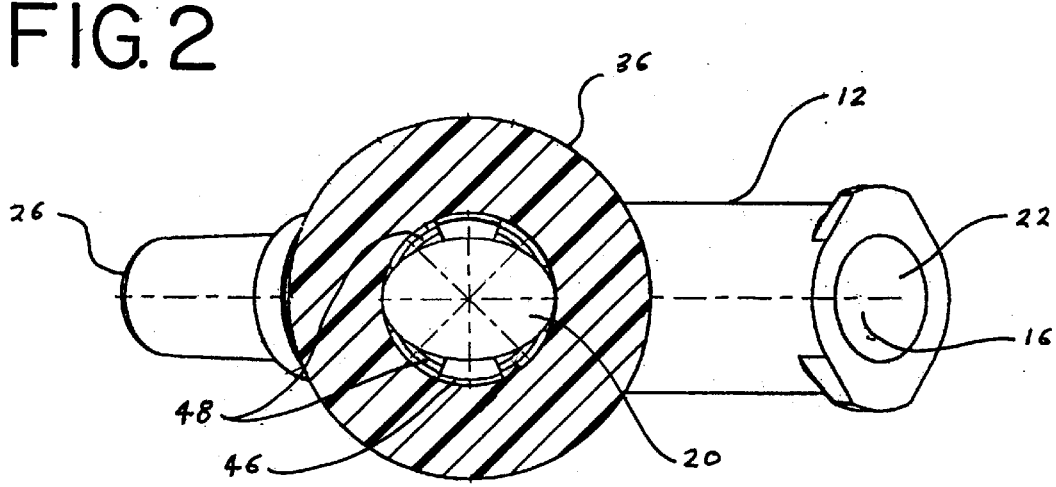
FIG. 2 is a cross-sectional view taken along line 2—2 of FIG. 1.

The injection access passageway 20 of the preferred embodiment is formed by the "Y"-leg 30 of the "Y"-adapter housing 12 and terminates in an injection access port 32 located at the exterior end of the injection access passageway 20. As best seen in FIG. 1, the needle-free access device 34 comprises a tubular body 36 and a cap 38. As best seen in FIG. 2, the interior surface of the tubular body 36 has a circular cross-section.

Figure 3:
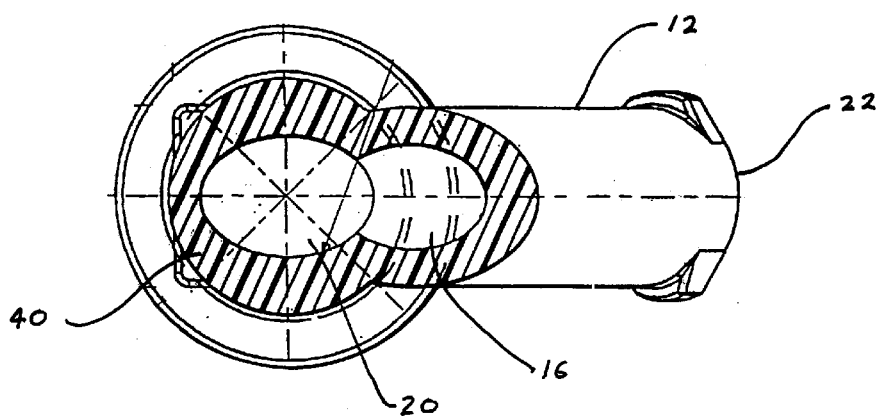
FIG. 3 is a cross-sectional view taken along line 3—3 of FIG. 1.

The portion of the "Y"-leg 30 which joins the tubular body 36 to that portion of the "Y"-adapter housing 12 which forms the inlet passageway 16 and the outlet passageway 18 is called the transition section 40. In other words, the transition section 40 is that portion of the injection access passageway 20 that is adjacent to the "Y"-site 14. As best seen in FIG. 3, the interior surface of the "Y"-leg 30 in the transition section 40 has a non-circular cross-section. In the preferred embodiment shown, the non-circular cross-section has an oval or elliptical shape. The oval or elliptical shape helps to prevent air from being trapped inside transition section 40 of the "Y"-leg 30 when the needle-free "Y"-adapter 10 is initially connected to the IV set tubing.

Referring to FIG. 1, the cap 38 comprises a channel 42 through the central portion of the cap 38. The channel 42 is tapered inwardly from the injection access port 32 so as to form a standard female luer. As will be explained in greater detail below, the size and configuration of the channel 42 is designed to mate with the end of a standard syringe.

A piston 44 is biased upwardly by a stretchable element, preferably a helical shaped spring coil 46, to fill the channel 42. The piston 44 is manufactured from a flexible material such as rubber. The lower end of the spring coil 46 is retained by a plurality of inwardly projecting nubs 48 spaced about the interior surface of the tubular body 36. In the embodiment shown, the inwardly projecting nubs 48 are located near the juncture between the tubular body 36 and the transition section 40.

The piston 44 of the preferred embodiment has a hole in its central portion which is filled by a pin 50, which is bonded to the soft material of the piston 44. The pin 50 provides rigidity to the piston 44, and transfers forces applied at the top of the pin 50 to the piston 44 and the connected spring coil 46. The top of the pin 50 is shaped to prevent occlusion of the end of the syringe or other device used to inject fluid through the needle-free access device 34. A wiper seal 52 is provided on the perimeter of the piston 44 near its top. The wiper seal 52 acts to seal the top of the channel 42 and injection access port 32 when the piston 44 is in its normal position. The wiper seal 52 also acts to clean the channel 42 and interior surface of the cap 38 after a fluid has been injected through the needle-free access device 34. Flow channels 54 are provided on the interior surface of the cap 38 near its bottom to permit fluids to pass around the wiper seal 52 when a syringe has been inserted into the injection access port 32.

The piston 44 also comprises an outwardly extending lip 56 near its bottom which seats against a sealing ring 58 on the lower portion of the cap 38 to form a valve to prevent fluids inside the "Y"-adapter from inadvertently leaking out through the injection access port 32. The lip 56 of the piston 44 also acts to retain the piston 44 and pin 50 inside the needle-free access device 34.

The needle-free access device 34 operates as follows. As a syringe (not shown) is inserted into the injection access port 32, the tip of the syringe contacts the top of the pin 50. As the tip of the syringe is forced into the channel 42, the spring coil 46 is compressed and the piston 44 and pin 50 are pushed downwards into the tubular body 36. The piston 44 and pin 50 are pushed downwards until the wiper seal 52 is just below the tops of the flow channels 54. In this position, the outside surface of a standard syringe is seated against the inside surface of the cap 38. The fluid being injected by the syringe then passes out the tip, over the top of the pin 50, through the flow channels 54, around the piston 44, and through the injection access passageway 20. The injected fluid is then mixed with the intravenous fluid passing through the "Y"-adapter 10 and subsequently administered to the patient. After the fluid is injected, the syringe is withdrawn from the injection access port 32. The spring coil 46 forces the piston 44 and pin 50 to move up into the channel 42 as the syringe tip is withdrawn.

In the alternative, other types of needle-free access devices can be incorporated into the "Y"-adapter of the present invention. For example, the "Y"-adapter of the present invention could incorporate any of the needle-free access devices disclosed in U.S. Pat. No. 5,360,413.

Although the preferred embodiment shown has a "Y"-shape, any configuration, such as a "T"-shape, can be used. However, the "Y"-shape is preferred because fluids being injected through the needle-free access device are directed in the a direction which coincides with the direction of flow of intravenous fluids passing through the "Y"-adapter housing 12 (i.e., through the inlet and outlet passageways, 16 and 18 respectively). Likewise, the interior surface of the "Y"-leg 30 could have a non-circular cross-section other than an oval or elliptical shape. For example, the interior surface of the "Y"-leg 30 could have a rectangular cross-section.

It should be appreciated that the apparatus of the present invention is capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

I claim:

1. A needle-free "Y"-adapter for use with intravenous delivery systems, said needle-free "Y"-adapter having a housing that comprises:

a) an inlet passageway which terminates at a proximal end in an inlet port;

b) an outlet passageway aligned with said inlet passageway and which terminates at a distal end in an outlet port; and c) an injection access passageway connected at a juncture to said inlet passageway at an angle, said injection access passageway terminating at a proximal end in an injection access port, said injection access passageway terminating at a distal end directly adjacent a distal end of said inlet passageway and comprising a needle-free access device, and an internal wall of said housing defines the distal end of said injection access passageway, wherein said internal wall has an oval or elliptical cross-section that assists to prevent air from being trapped inside the housing at the juncture when the adapter is initially connected to the intravenous delivery system.

2. A needle-free "Y"-adapter according to claim 1 wherein said housing comprises a "Y"-shaped housing having a first leg, a second leg, and a third leg, said first leg forming said inlet passageway, said second leg forming said outlet passageway, and said third leg forming said injection access passageway.

3. A needle-free "Y"-adapter according to claim 1 wherein said inlet passageway and said outlet passageway are axially aligned on a common central axis.

4. A needle-free "Y"-adapter according to claim 3 wherein the juncture of the connection of said injection access passageway to said inlet passageway forms an acute angle.

5. A needle-free "Y"-adapter according to claim 3 wherein the juncture of the connection of said injection access passageway to said inlet passageway and said outlet passageway forms a right-angle.

6. A needle-free "Y"-adapter according to claim 1 wherein said inlet port and said outlet port are each configured to connect to IV set tubing.

7. A needle-free "Y"-adapter according to claim 1 wherein the internal wall of said housing of said injection access passageway has a cross-section of oval or elliptical shape.

8. A needle-free "Y"-adapter according to claim 1 wherein said needle-free access device comprises a valve formed by a movable piston biased against a valve seat, said movable piston being biased against said valve seat by a coil spring.

9. A needle-free "Y"-adapter according to claim 8 wherein said needle-free access device further comprises a wiper seal, said wiper seal being formed by said movable piston.

10. A needle-free "Y"-adapter for use with intravenous delivery systems comprising:
    a) a "Y"-shaped housing having an inlet passageway, an outlet passageway, and an injection access passageway, each of said passageways being defined by an internal wall of said housing and comprising an interior end and an exterior end, wherein said interior ends of said passageways are in fluid communication and intersect with each other at a common juncture, further wherein the internal wall of said housing that defines said injection access passageway comprises an oval or elliptical cross-section at said juncture to assist in preventing air from being, trapped inside the housing when the adapter is initially connected to the intravenous delivery system;
    b) an inlet port located at said exterior end of said inlet passageway;
    c) an outlet port located at said exterior end of said outlet passageway;
    d) an injection access port located at said exterior end of said injection access passageway; and
    e) a needle-free access device located in said injection access passageway adjacent to said injection access port.

11. A needle-free "Y"-adapter according to claim 10 wherein said inlet port and said outlet port are each configured to connect to IV set tubing.

12. A needle-free "Y"-adapter according to claim 10 wherein said needle-free access device comprises a valve formed by a movable piston biased against a valve seat, said movable piston being biased against said valve seat by a coil spring.

13. A needle-free "Y"-adapter according to claim 12 wherein said needle-free access device further comprises a wiper seal, said wiper seal being formed by said movable piston.

14. A needle-free "Y"-adapter for use with intravenous delivery systems, said needle-free "Y"-adapter having a "Y"-shaped housing that comprises:
    a) an inlet passageway which terminates at a proximal end in an inlet port, said inlet port being configured to connect to IV set tubing;
    b) an outlet passageway axially aligned with said inlet passageway and which terminates at a distal end in an outlet port, said outlet port being configured to connect to IV set tubing:
    c) an injection access passageway connected at a juncture to said inlet passageway at an acute angle, said injection access passageway terminating at a proximal end in an injection access port, said injection access port comprising a female luer, said injection access passageway terminating at a distal end directly adjacent a distal end of said inlet passageway and comprising a needle-free access device, and an internal wall of said housing defines the distal end of said injection access passageway, wherein said internal wall has a cross-section of oval or elliptical shape that assists to prevent air from being trapped inside the housing at the juncture when the adapter is initially connected to the intravenous delivery system, and
    d) a needle-free access device located in said injection access passageway adjacent to said injection access port, said needle-free access device comprising a valve formed by a movable piston biased against a valve seat, said movable piston being biased against said valve seat by a coil spring.

* * * * *